(12) United States Patent
Yim et al.

(10) Patent No.: US 8,809,578 B2
(45) Date of Patent: Aug. 19, 2014

(54) COMPOUND RAMALIN AND USE THEREOF

(75) Inventors: Joung Han Yim, Seongnam-si (KR); Hong Kum Lee, Ansan-si (KR); Hari Datta Bhattarai, Goettingen (DE); Paudel Babita, Goettingen (DE); Il Chan Kim, Seoul (KR); Soon Gyu Hong, Seoul (KR); Doc Kyu Kim, Incheon (KR); Yoo Kyung Lee, Seoul (KP); Sung Gu Lee, Incheon (KR); Hyun Cheol Oh, Busan (KR)

(73) Assignee: Korea Ocean Research and Development Institute, Incheon (KR)

( * ) Notice: Subject to any disclaimer, the term of this patent is extended or adjusted under 35 U.S.C. 154(b) by 208 days.

(21) Appl. No.: 13/128,586

(22) PCT Filed: Nov. 10, 2009

(86) PCT No.: PCT/KR2009/006562
§ 371 (c)(1),
(2), (4) Date: Jul. 18, 2011

(87) PCT Pub. No.: WO2010/053327
PCT Pub. Date: May 14, 2010

(65) Prior Publication Data
US 2011/0262374 A1  Oct. 27, 2011

(30) Foreign Application Priority Data
Nov. 10, 2008 (KR) .................. 10-2008-0111021

(51) Int. Cl.
*A61Q 19/02* (2006.01)
*A61Q 19/08* (2006.01)
*A23L 1/29* (2006.01)
*A61K 8/42* (2006.01)
*C07C 243/34* (2006.01)

(52) U.S. Cl.
CPC .............. *C07C 243/34* (2013.01); *A23L 1/29* (2013.01); *A61Q 19/02* (2013.01); *A61Q 19/08* (2013.01); *A61K 2800/522* (2013.01); *A23V 2002/00* (2013.01); *A61K 8/42* (2013.01)
USPC .......... 562/400; 562/433; 562/439; 562/443; 562/450; 424/69; 424/195.15; 514/150; 514/579; 514/614; 514/615; 514/626; 514/629; 514/646; 564/123; 564/148; 564/149; 564/151

(58) Field of Classification Search
USPC .......... 562/400, 433, 439, 443, 450; 564/123, 564/148, 149, 151; 514/150, 579, 614, 615, 514/626, 629, 646; 424/69, 195.5, 195.16
See application file for complete search history.

(56) References Cited

U.S. PATENT DOCUMENTS

| | | | | |
|---|---|---|---|---|
| 3,092,546 A | * | 6/1963 | Schroeter et al. | 514/328 |
| 3,288,848 A | * | 11/1966 | Hinman et al. | 562/439 |
| 3,759,794 A | * | 9/1973 | Sax | |
| 2013/0116324 A1 | * | 5/2013 | Yim et al. | 514/563 |

FOREIGN PATENT DOCUMENTS

| | | |
|---|---|---|
| JP | 5246876 A | 9/1993 |
| KR | 1998-0008216 A | 4/1998 |

OTHER PUBLICATIONS

Bhattarai et al., Thin layer chromatography analysis of antioxidant constituents of lichens from Antarctica, 2008, J. Nat. Med., 62:481-484.*
K. Muller, Pharmaceutically relevant metabolites from lichens, 2001, Appl. Microbiol. Biotechnol., 56:9-16.*
Behera et al., Determination of antioxidative potential of lichen *Usnea ghattensis* in vitro, 2006, Lebensm. Wiss. Technol., 39:80-85.*
Gulluce et al., Screening the antioxidant and antimicrobial properties of the lichens *Parmelia saxatilis, Platismatica glauca, Ramalina pollinaria, Ramalina polymorpha* and *Umbilicaria nylanderiana*, 2006, Phytomedicine, 13:515-521.*
Merriam-Webster Dictionary Online, Prevention—definition [online], [retrieved Jan. 14, 2013]. Retrieved from the Internet <URL: http://www.merriam-webster.com/dictionary/prevention>.*
Bhattari et al., "Thin layer chromatography analysis of antioxidant constituents of lichens from Antarctica," 2008, J. Nat. Med., 62:481-484.*

K. Muller, "Pharmaceutically relevant metabolites from lichens," 2001, Appl. Microbiol. Biotechnol., 56:9-16.*

Roullier et al., "Multiple dual-mode centrifugal partition chromatography as an efficient method for the purification of a mycosporine from a crude methanolic extract of *Lichina pygmaea*", Feb. 2009, Journal of Chromatography B, 877:2067-2073.*

Gulluce et al., "Screening the antioxidant and antimicrobial properties of the lichens *Parmelia saxatilis, Platismatica glauca, Ramalina pollinaria, Ramalina polymorpha* and *Umbilicaria nylanderiana*," 2006, Phytomedicine, 13:515-521.*

Bhattarai et al., "Thin-layer chromatography analysis of antioxidant constituents of lichens from Antarctica", 2008, J. Nat. Med., 62: 481-484.*

Roullier et al., "Multiple dual-mode centrifugal partitiion chromatography as an efficient method for the purification of a mycosporine from a crude methanolic extract of Lichina pygmaea," Feb. 2009, Journal of Chromatography B, 877: 20672073.*

K. Muller, "Pharmaceutically relevant metabolites from lichens," 2001, Appl. Microbiol. Biotechnol., 56: 9-16.*

Gulluce et al., "Screening the antioxidant and antimicrobial properties of the lichens *Parmelia saxatilis, Platismatica glauca, Ramalina pollinaria, Ramalina polymorpha*, and *Umbilicaria nylanderiana*," 2006, Phytomedicine, 13: 515-521.*

Paudel et al., Antioxidant activity of polar lichens from King George Island (Antarctica), 2008, Polar Biology, 31:605-608.*

Roullier et al., "A novel aryl-hydrazide from the marine licen *Lichina pygmaea*: Isolation, synthesis of derivatives, and cytotoxicity assays," 2010, Bioorganic & Medicinal Chemistry Letters, 20:4582-4586 (for reference purposes only; not part of rejections).*

Paudel et al., Antioxidant activity of polar lichens from King George Island (Antarctica), 2008, Polar Biology, 31: 605-608.*

Roullier et al., "A novel aryl-hydrazide from the marine lichen *Lichina pygmaea*: Isolation, synthesis of derivatives, and cytotoxicity assays," 2010, Bioorganic & Medicinal Chemistry Letters, 20: 4582-4586.*

Kinoshita, et al., The Synthesis of Anthglutin and Its Analogues, Bulletin of the Chemical Society of Japan, vol. 54, pp. 2219-2220, 1981.

International Search Report, International Application No. PCT/KR2009/006562 dated May 25, 2010—3 pages.

Ames, B.N. et al., Oxidants, antioxidants, and the degenerative diseases of aging, Proc. Natl. Acad. Sci. USA, vol. 90, pp. 7915-7922, Sep. 1993.

Dean, R. T. et al., Reactive species and their accumulation on radical-damaged proteins, Trends. Biochem..Sci., vol. 18, pp. 437-441, Nov. 1993.

Tseng, T.H. et al., Protective Effects of Dried Flower Extracts of *Hibiscus sabdariffa* L against Oxidative Stress in Rat Primary Hepatocytes, Food and Chemical Toxicology, vol. 35, pp. 1159-1164, 1997.

Shimizu, et al., Novel Vitamin E Derivative with 4-Substituted Resorcinol Moiety Has Both Antioxidant and Tyrosinase Inhibitory Properties, Lipids, vol. 36, No. 12, pp. 1321-1326, 2001.

Grice, H. C., Safety Evaluation of Butylated Hydroxyanisole from the perspective of effects on forestomach and oesophageal squamous epithelium, Food. Chem. Toxico. vol. 26, No. 8, pp. 717-723, 1988.

Velioglu, Y.S. et al., Antioxidant Activity and Total Phenolics in Selected Fruits, Vegetables, and Grain Products, J. Agric. Food Chem., vol. 46, pp. 4113-4117, 1998.

Ahmadjian, Vernon, The Lichen Symbiosis, Wiley, New York, pp. 1-7, 1993.

Behera, B.C. et al., Determination of antioxidative potential of lichen *Usnea ghattensis* in vitro, Lebensm. Wiss. Technol., vol. 39, pp. 80-85, 2006.

Müller, K., Pharmaceutically relevant metabolites from lichens, Appl. Microbiol. Biotechnol., vol. 56, pp. 9-16, 2001.

Bhattarai, H.D. et al., Thin layer chromatography analysis of antioxidant constituents of lichens from Antarctica, J. Nat. Med., vol. 62, pp. 481-484, 2008.

* cited by examiner

*Primary Examiner* — Jane C Oswecki

(74) *Attorney, Agent, or Firm* — Knobbe, Martens, Olson & Bear, LLP

(57) ABSTRACT

The present invention relates to a novel compound having excellent antioxidant activity, isolated from *Ramalina terebrata*, and more particularly to a novel compound, RAMALIN™, having excellent antioxidant activity, isolated from the Antarctic lichen *Ramalina terebrata*, a method for preparing the RAMALIN™, and a pharmaceutical composition, a functional food and a functional cosmetic composition, which contain the RAMALIN™ as an active ingredient. The RAMALIN™ according to the invention has significantly excellent antioxidant effects compared to commercially available antioxidants, and thus can be widely used in agents for treating oxidation-related diseases, anti-aging functional foods, functional cosmetic products for skin whitening and wrinkle reduction, etc.

6 Claims, 10 Drawing Sheets

COMPOUND RAMALIN AND USE THEREOF

TECHNICAL FIELD

The present invention relates to a novel compound having excellent antioxidant activity, isolated from *Ramalina terebrata*, and more particularly to a novel compound, RAMALIN™, having excellent antioxidant activity, isolated from the Antarctic lichen *Ramalina terebrata*, a method for preparing the RAMALIN™, and a pharmaceutical composition, a functional food and a functional cosmetic composition, which contain the RAMALIN™ as an active ingredient.

BACKGROUND ART

Organisms accumulate reactive oxygen species (hereinafter referred to as "ROS") and reactive nitrogen species during their normal metabolic process and from external sources. ROS, including superoxide anion ($O_2$), hydroxyl radical (OH), hydrogen peroxide ($H_2O_2$) and hypocholorous acid (HOCl), are involved in inflammation, cardiovascular diseases, cancers, aging-related diseases, metabolic diseases and atherosclerosis (Ames, B. N. et al., *Proc. Natl. Acad. Sci. USA*, 90:7915, 1993). ROS attack unsaturated fatty acids to cause the lipid peroxidation of the cell membrane, reduce the permeability of the membrane, reduce the activity of enzyme receptors, and cause damage to cell membrane proteins, thus causing cell inactivation (Dean, R. T. and Davies, M. J., *Trends. Biochem. Sci.*, 18:437, 1993).

Organisms have natural defense mechanisms against the toxicity of ROS; nevertheless, the increase in the accumulation of ROS during the life of cells can cause irreversible oxidative damage to the cells (Tseng, T. H. et al., *Food Chem. Toxicol.*, 35:1159, 1997). For this reason, antioxidants that eliminate free radical intermediates to delay or suppress oxidation processes have been requested. Although several potent synthetic antioxidants were already developed (Shimizu, K. et al., *Lipids,* 36:1321, 2001), these were shown to be highly potent carcinogens (Wichi, H. P. et al., *Food Chem. Toxicol.* 26:717-72, 1988). For this reason, the need to isolate antioxidants for use as health supplements from natural sources has been addressed. A wide range of natural substances, including phenolic compounds, nitrogen compounds and carotenoids, have antioxidant activity (Velioglu, Y. S. et al., *J. Agric. Food Chem.*, 46:113, 1998).

Lichens are similar to non-flowering plants and are the symbiotic association of fungi (mycobionts) with algae and/or cyanobacteria (photobionts). The fungi in lichens form thalli or lichen substrates containing typical secondary metabolites (Ahmadjin, V. *The lichen symbiosis*. Wiley, New York, pp. 1-6, 1993). It is difficult to obtain sufficient amounts of natural lichen samples, and technology of cultivating large amounts of lichens is not known. For this reason, studies on lichens were insufficient compared to studies on higher plants. As the tissue culture method, mass-production method and biochemical analysis method for lichens have been improved, studies thereon have been actively conducted (Behera, B. C. et al., *Lebensm. Wiss. Technol.*, 39:805, 2006). Compounds having various biological activities (including cytotoxicity, antifungal, antimicrobial, antioxidant and anti-inflammatory activities), including fatty acids, depsides, depsidones, dibenzofurans, diterpenes, anthraquinones, naphtoquinones, usninic acid, pulvinic acids, xanthones and epidithiopiperazinediones, were isolated from lichens (Müller, K., *Appl. Microbiol. Biotechnol.*, 56:9-16, 2001). Lichens known to have antioxidant activity are mostly species of tropical and subtropical origin. Studies on the antioxidant activity of polar lichens are still insufficient (Bhattarai, H. D. et al., *J. Nat. Med.*, 62:481, 2008).

Accordingly, the present inventors have made many efforts to isolate a novel compound having antioxidant activity from Antarctic lichens having various antioxidant activities and, as a result, have isolated the novel compound RAMALIN™ having very high antioxidant activity from the Antarctic lichen *Ramalina terebrata* having various antioxidant activities, thereby completing the present invention.

DISCLOSURE OF INVENTION

It is an object of the present invention to provide a novel compound, RAMALIN™, derived from *Ramalina terebrata*, and a preparation method thereof.

Another object of the present invention is to provide an antioxidant composition containing the RAMALIN™ as an active ingredient.

Still another object of the present invention is to provide a functional food and a functional cosmetic composition, each containing the RAMALIN™ as an active ingredient.

To achieve the above objects, the present invention provides a compound (RAMALIN™) having a structure of the following formula 1:

[Formula 1]

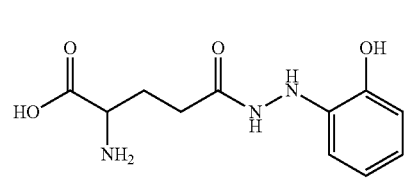

The present invention also provides a method for preparing a compound (RAMALIN™) having a structure of formula 1, the method comprising the steps of:

(a) extracting dried *Ramalina terebrata* with a polar solvent selected from water, a $C_1$-$C_4$ lower alcohol and a mixed solvent thereof, thereby obtaining a crude extract;

(b) extracting the crude extract with a non-polar solvent selected from hexane, chloroform, benzene, carbon tetrachloride and pentane, thereby removing a non-polar solvent fraction which is extracted with the non-polar solvent; and (c) subjecting the extract, from which the non-polar solvent fraction has been removed, to liquid chromatography, thereby obtaining a fraction showing antioxidant activity.

The present invention also provides an antioxidant composition containing, as an active ingredient, a compound (RAMALIN™) having a structure of formula 1.

The present invention also provides a pharmaceutical composition for prevention or treatment of oxidation-related disease, the composition comprising, as an active ingredient, a compound (RAMALIN™), having a structure of formula 1, or a pharmaceutically acceptable salt thereof, together with a pharmaceutically acceptable carrier or excipient.

The present invention also provides a functional food and a functional cosmetic composition, each containing, as an active ingredient, a compound (RAMALIN™) having a structure of formula 1.

BEST MODE FOR CARRYING OUT THE INVENTION

Figure 1:
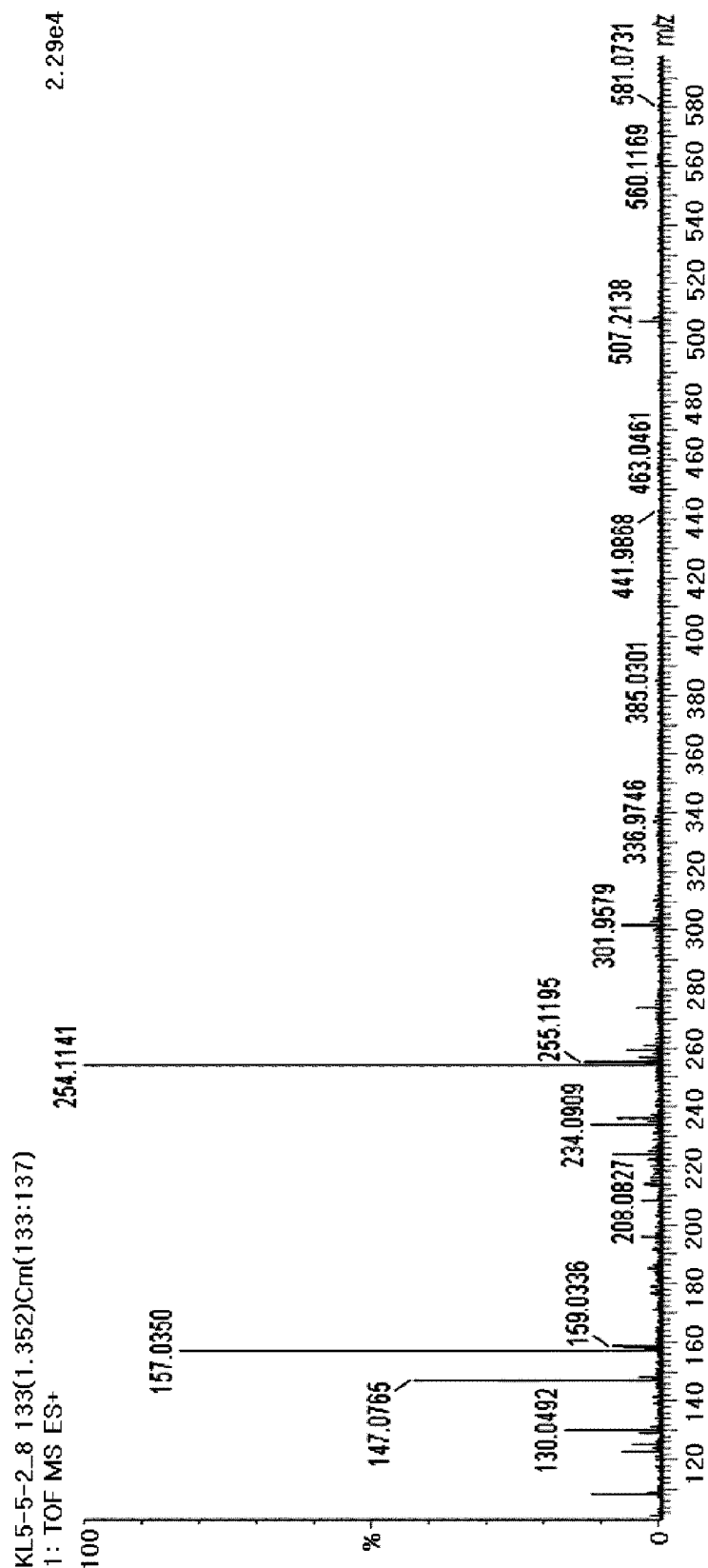
FIG. 1 shows the high-resolution ESI-MS spectrum of the RAMALIN™ according to the present invention.

In one aspect, the present invention is directed to a compound (RAMALIN™) having a structure of the following formula 1:

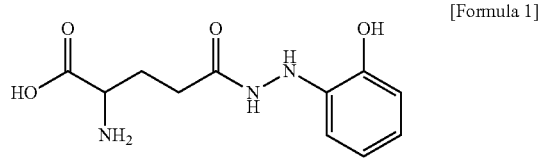 [SMILES: NC(CCC(=O)NNc1ccccc1O)C(=O)O]

[Formula 1]

RAMALIN™ of the present invention is a novel compound, having antioxidant activity, isolated from the Antarctic lichen *Ramalina terebrata*. The high-resolution ESI-MS, $^1$H NMR and $^{13}$C NMR spectra of the RAMALIN™ indicated that the RAMALIN™ has a molecular weight of 254.1141 and is a compound having a molecular formula of $C_{11}H_{16}N_3O_4$ as shown in formula 1. The name "RAMALIN™" was given because it is a compound isolated from *Ramalina terebrata*.

In another aspect, the present invention is directed to a method for preparing a compound (RAMALIN™) having a structure of formula 1, the method comprising the steps of:

(a) extracting dried *Ramalina terebrata* with a polar solvent selected from water, a $C_1$-$C_4$ lower alcohol and a mixed solvent thereof, thereby obtaining a crude extract;

(b) extracting the crude extract with a non-polar solvent selected from hexane, chloroform, benzene, carbon tetrachloride and pentane, thereby removing a non-polar solvent fraction which is extracted with the non-polar solvent; and (c) subjecting the extract, from which the non-polar solvent fraction has been removed, to liquid chromatography, thereby obtaining a fraction showing antioxidant activity.

In one Example of the present invention, the RAMALIN™ was obtained in the following manner. *Ramalina terebrata* was cold-extracted with a mixed solution of methanol:water (70:30 v/v) and hot-extracted, thus obtaining a crude extract. The obtained crude extract was extracted with hexane to remove pigments of low polarity, and the remaining liquid phase was extracted with chloroform to remove compounds of low or moderate polarity. The remaining water-soluble extract was fractioned using a gradient solvent system consisting of solutions of methanol in water. As a result, the extract in the 0% methanol solution showed activity ($IC_{50}=8$ µg/mL) against most DPPH free radicals. The active fraction was purified twice by semi-preparative reverse-phase HPLC using a C18ODS column with different solvents.

In still another aspect, the present invention is directed to an antioxidant composition containing, as an active ingredient, a compound (RAMALIN™) having a structure of formula 1.

In the present invention, in order to examine the antioxidant activity of the RAMALIN™, the DPPH free-radical scavenging activity, ABTS free-radical scavenging activity, $Fe^{+3}$-reducing activity, superoxide radical scavenging activity and tyrosinase inhibitory activity of the RAMALIN™ were analyzed. The analysis results are summarized in Table 1 below. As shown in Table 1, the DPPH free-radical scavenging activity of the RAMALIN™ was about 5 times higher than that of the commercially available antioxidant BHA (butylated hydroxyanisole), and ABTS free-radical scavenging activity thereof was about 27 times higher than that of the vitamin E analogue Trolox. Also, the ability of the RAMALIN™ to reduce $Fe^{+3}$ ions to $Fe^{+2}$ ions was about 25 times higher than that of the commercially available antioxidant BHT (butylated hydroxytoluene). In addition, the superoxide radical scavenging activity of the RAMALIN™ was 1.2 times higher than that of ascorbic acid.

Furthermore, the tyrosinase inhibitory activity of the RAMALIN™ was 1.25 times higher than that of commercially available kojic acid, indicating that the RAMALIN™ shows an excellent skin whitening effect.

TABLE 1

Comparison of antioxidant activity of RAMALIN™ with commercially available antioxidants

| commercially available antioxidants | $IC_{50}$ concentration (µg/mL) | | | | |
|---|---|---|---|---|---|
| | DPPH (µg/mL) | ABTS (µg/mL) | Superoxide (µg/mL) | Tyrosinase activity (µg/mL) | Reducing Power (1 µg of BHT equivalent) |
| L5-5-2 | 0.99 ± 0.08 | 1.7 ± 0.2 | 10.2 ± 1.2 | 4 ± 0.4 | 0.04 ± 0.003 |
| BHA | 4.97 ± 0.9 | — | — | — | — |
| Trolox | — | 46.35 ± 5.1 | — | — | — |
| Ascorbic acid | — | — | 12.7 ± 1.2 | — | — |
| Kojic acid | — | — | — | 5 ± 0.5 | — |

Also, the RAMALIN™ showed the effect of inhibiting $H_2O_2$ and NO production in macrophages.

Figure 9:
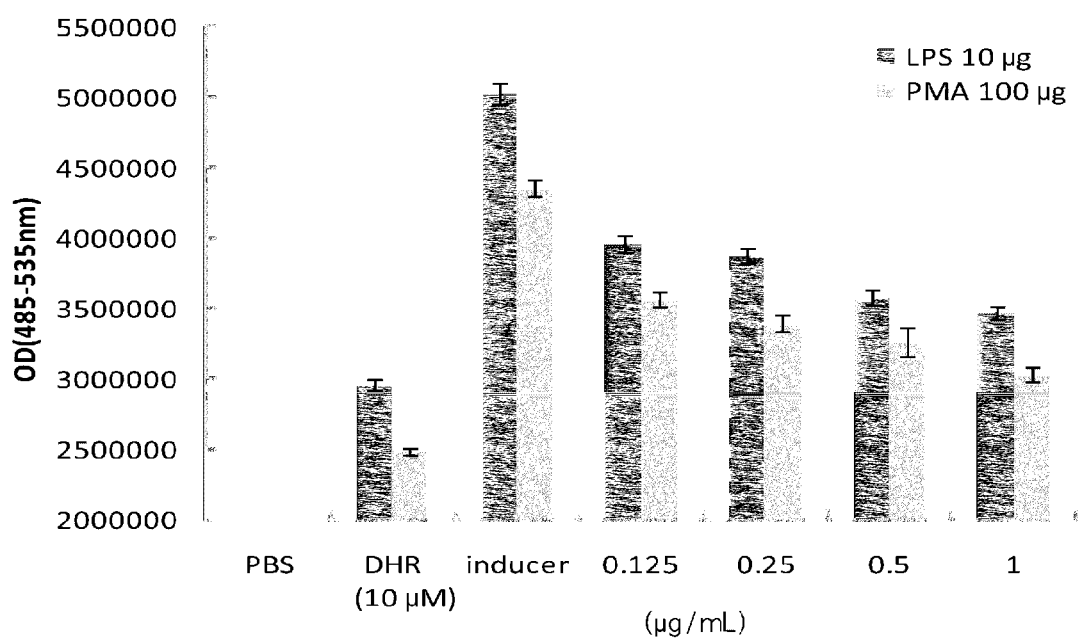
FIG. 9 shows the results of analyzing the ability of the RAMALIN™ to inhibit $H_2O_2$ production in Raw 264.7 cells activated with LPS or PMA.
Figure 10:
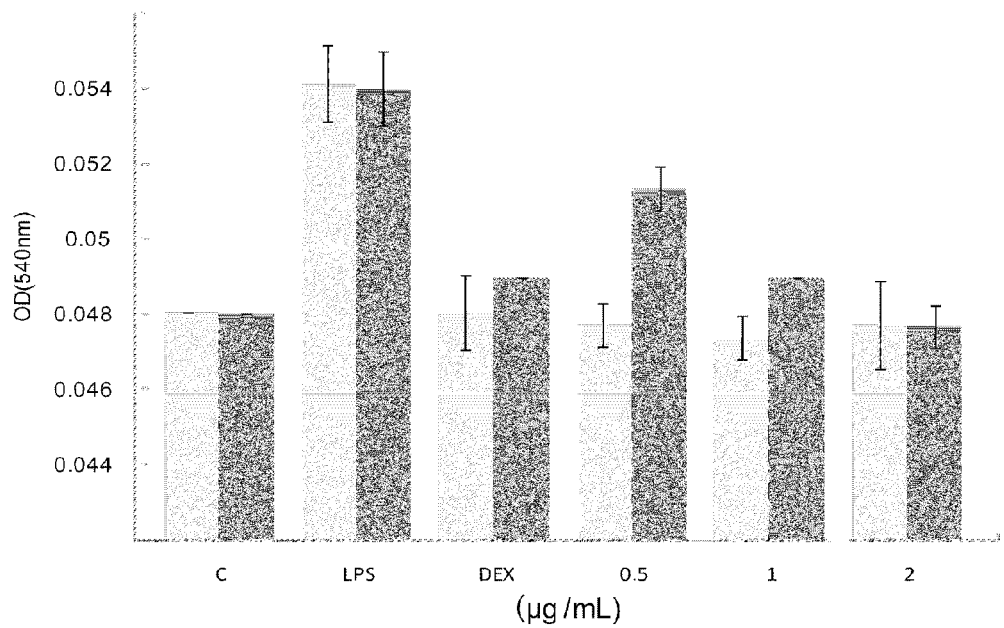
FIG. 10 shows the results of analyzing the ability of the RAMALIN™ to inhibit NO production in Raw 264.7 cells activated with LPS.

In one Example of the present invention, mouse macrophage cells were treated with the RAMALIN™. As a result, it could be seen that the production of $H_2O_2$ and NO in the cells treated with the RAMALIN™ was significantly inhibited (FIGS. 9 and 10).

In yet another aspect, the present invention is directed to a pharmaceutical composition for prevention or treatment of oxidation-related disease, the composition comprising, as an active ingredient, a compound (RAMALIN™), having a structure of formula 1, or a pharmaceutically acceptable salt thereof, together with a pharmaceutically acceptable carrier or excipient.

As used herein, the term "oxidation-related disease" is meant to include cancer, aging, coronary arteriosclerosis, diabetes, epilepsy, and neurodegenerative disease.

The pharmaceutical composition according to the present invention can be administered by various routes, including, but not limited to, oral, intravenous, intramuscular, intra-arterial, intramedullary, intradural, intracardial, transdermal, subcutaneous, intraperitoneal, intranasal, gastrointestinal, local, sublingual and rectal routes. Preferably, the composition of the present invention is administered orally or parenterally. As used herein, the term "partenteral" includes subcutaneous, intradermal, intravenous, intramuscular, intraperitoneal, intra-articular, intra-synovial, intrasternal, intrathecal, intralesional and intracranial injection or infusion techniques. The pharmaceutical composition of the present invention may also be administered in the form of suppositories for rectal administration.

The pharmaceutical composition of the present invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The dose level of the pharmaceutical composition of the present invention will depend upon a variety of factors, including the activity of the specific compound employed, the age, body weight, general health status, sex, diet, time of administration, rate of excretion, drug combination, and the severity of the particular disease to be prevented or treated. The pharmaceutical composition according to the present invention can be formulated in the form of pills, sugar-coated tablets, capsules, liquid, gel, syrup, slurry or suspensions.

In a further aspect, the present invention is directed to a functional food containing, as an active ingredient, a compound (RAMALIN™) having a structure of formula 1.

The functional food of the present invention can be used in various applications, including drugs, foods and beverages. Examples of the functional food of the present invention include various foods, candies, chocolates, beverages, gums, teas, vitamin complexes, health supplement foods, and the like, and it can be used in the form of powders, granules, tablets, capsules or beverages.

The extract of the present invention may be added to foods or beverages for prevention of diabetes and obesity. With respect to the content of the extract in food or a beverage, the extract of the present invention may generally be added in an amount of 0.01-50 wt %, and preferably 0.1-20 wt %, based on the total weight of the health functional food of the present invention, and the extract of the present invention may be added in an amount of 0.02-10 g, and preferably 0.3-1 g, based on 100 ml of the health beverage composition of the present invention.

Providing that the health beverage composition of the present invention comprises the extract as an essential ingredient, there is no particular limitation in other liquid components of the beverage composition, and the composition may further comprise one or more additives, such as various flavors or natural carbohydrates which are commonly used in beverages. Examples of natural carbohydrates for such purposes include common sugars such as monosaccharides, for example, glucose, fructose and the like; disaccharides, for example, maltose, sucrose and the like; and polysaccharides, for example, dextrine, cyclodextrine and the like, and sugar alcohols such as xylitol, sorbitol, erythritol and the like. In addition to the foregoing, as the flavors, natural flavors (thaumatin, stevia extract (for example, Rebaudioside A, glycyrrhizin and the like), and synthetic flavors (saccharine, aspartame and the like) may be advantageously used. The content of the natural carbohydrate in the composition of the present invention is about 1-20 g, and preferably about 5-12 g, based on 100 ml of the composition.

In addition, the composition of the present invention may further contain various nutrients, vitamins, minerals (electrolytes), seasonings (artificial seasonings and natural seasonings), coloring agents and improving agents (cheese, chocolate and the like), pectic acid and salts thereof, alginic acid and salts thereof, organic acids, protective colloid thickeners, pH controllers, stabilizers, preservatives, glycerin, alcohols, carbonating agents used in carbonated beverages, and the like. In addition, the composition of the present invention may further contain fruit fresh for preparation of natural fruit juice beverages, fruit juice beverages and vegetable beverages. These additives may be used independently or in combination. Although the content of these additives in the composition of the present invention is not particularly important to the present invention, it is generally selected within the range of 0-20 parts by weight based on 100 parts by weight of the composition of the present invention.

In a further still aspect, the present invention is directed to a functional cosmetic composition containing, as an active ingredient, a compound (RAMALIN™) having a structure of formula 1.

The functional cosmetic composition of the present invention may be formulated into conventional emulsions and solubilized formulations. The emulsion-type cosmetic formulations include milk lotion, cream, essence and the like, and the solubilized cosmetic formulations include skin lotion.

Examples of cosmetic formulations suitable for the present invention include solutions, gels, anhydrous solids or pastes, oil-in-water emulsions, suspensions, microemulsions, microcapsules, microgranules, ionic (liposomes) or non-ionic vesicular dispersions, creams, skin lotions, powders, ointments, sprays and concealing sticks. In addition, foam formulations and aerosol formulations containing compressed propellants are contemplated as possible formulations.

In addition, the cosmetic composition of the present invention may further comprise adjuvants that are conventionally used in the cosmetic and dermatological field. Examples of such adjuvants include fats, organic solvents, solubilizer, thickeners, gelling agents, softeners, antioxidants, suspending agents, stabilizers, foaming agents, aromatics, surfactants, water, ionic or non-ionic emulsifiers, fillers, metal ion sequesterers and chelators, preservatives, vitamins, screening agents, humectants, essential oils, dyes, pigments, hydrophilic or lipophilic activating agents and lipid vesicles. These adjuvants may be introduced in amounts that are conventionally used in the dermatological field.

The functional cosmetic composition of the present invention has excellent antioxidant activity, high storage stability and an excellent effect of whitening skin and reducing skin wrinkles, and thus can advantageously used as a functional cosmetic product for preventing skin aging.

EXAMPLES

Hereinafter, the present invention will be described in further detail with reference to examples. It will be obvious to a person having ordinary skill in the art that these examples are illustrative purposes only and are not to be construed to limit the scope of the present invention. That is, the following steps will be described as one illustrative ones and do not limit the scope of the present invention.

Example 1

High-Throughput Extraction of *Ramalina terebrata*

*Ramalina terebrata* is a lichen that grows naturally in the Antarctic King George Island and can be easily collected through the King George Island.

672 g of a completely freeze-dried and ground lichen *Ramalina terebrata* sample was cold-extracted with a mixed solution of methanol:water (70:30 v/v) at room temperature, and then hot-extracted in a water bath at 45-50° C. The extract was filtered, and then evaporated under vacuum at 45° C. to remove the solvent. The above extraction process was repeated three times to obtain all extractable compounds. The resulting extract was freeze-dried, thereby obtaining 83 g of a crude extract. The obtained crude extract was stored at −20° C. until use.

Example 2

Purification and Structural Analysis of RAMALIN™

The crude extract obtained in Example 1 was dissolved in 1 liter of distilled water, and then extracted three times with 1 liter of hexane to remove pigments of low polarity. The remaining liquid phase was extracted three times with 1 liter of chloroform to remove compounds of low or moderate polarity. The remaining water-soluble extract showed a high scavenging activity of $IC_{50}=9$ μg/mL against DPPH free radicals and was subjected to automated MPLC (mild pressure liquid chromatography) using a C180DS column (150 cm×3 cm). The extract was fractioned using a gradient solvent system consisting of 0%, 20%, 40%, 60%, 80% and 100% solutions of methanol in water. As a result, the extract in the 0% methanol solution showed activity ($IC_{50}=8$ μg/mL) against most DPPH free radicals. The active fraction was subjected to semi-preparative reverse-phase HPLC at a flow rate of 2 ml/min, and the solvent system used in the chromatography is shown in Table 2 below.

TABLE 2

Solvent system used in first semi-preparative reverse-phase HPLC

| Minute | H₂O(0.1% formic acid) | Methanol |
| --- | --- | --- |
| 10 | 100% | 0% |
| 20 | 80% | 20% |
| 30 | 0% | 100% |
| 40 | 0% | 100% |

As a result, the active fraction showed activity ($IC_{50}=1$ μg/mL) against most DPPH free radicals at the fifth peak at 18.88 minutes. The active fraction was additionally subjected to semi-preparative reverse-phase HPLC at a flow rate of 2 ml/min using a C180DS column (250 cm×10 cm), and the solvent system used in the chromatography is shown in Table 3 below.

TABLE 3

Solvent system used in second semi-preparative HPLC

| Minute | H₂O(0.1% formic acid) | Acetonitrile | Methanol |
| --- | --- | --- | --- |
| 0 | 90% | 10% | 0% |
| 30 | 50% | 50% | 0% |
| 31 | 0% | 100% | 0% |

As a result, the second fraction obtained at 8.26 minutes showed an activity of $IC_{50}=0.99$ μg/mL against DPPH free radicals and was named "RAMALIN™ Ramalin". The structure of the fraction was analyzed.

Example 3

Structural Analysis of RAMALIN™

Both positive and negative modes of high-resolution ESI-MS were used to detect the fragmentation pattern of the compound. Also, in $D_2O+$Acetone $d_6$, $^1H$ NMR and $^{13}C$ NMR (400 MHz) were performed to confirm the final structure of the compound.

Figure 2:
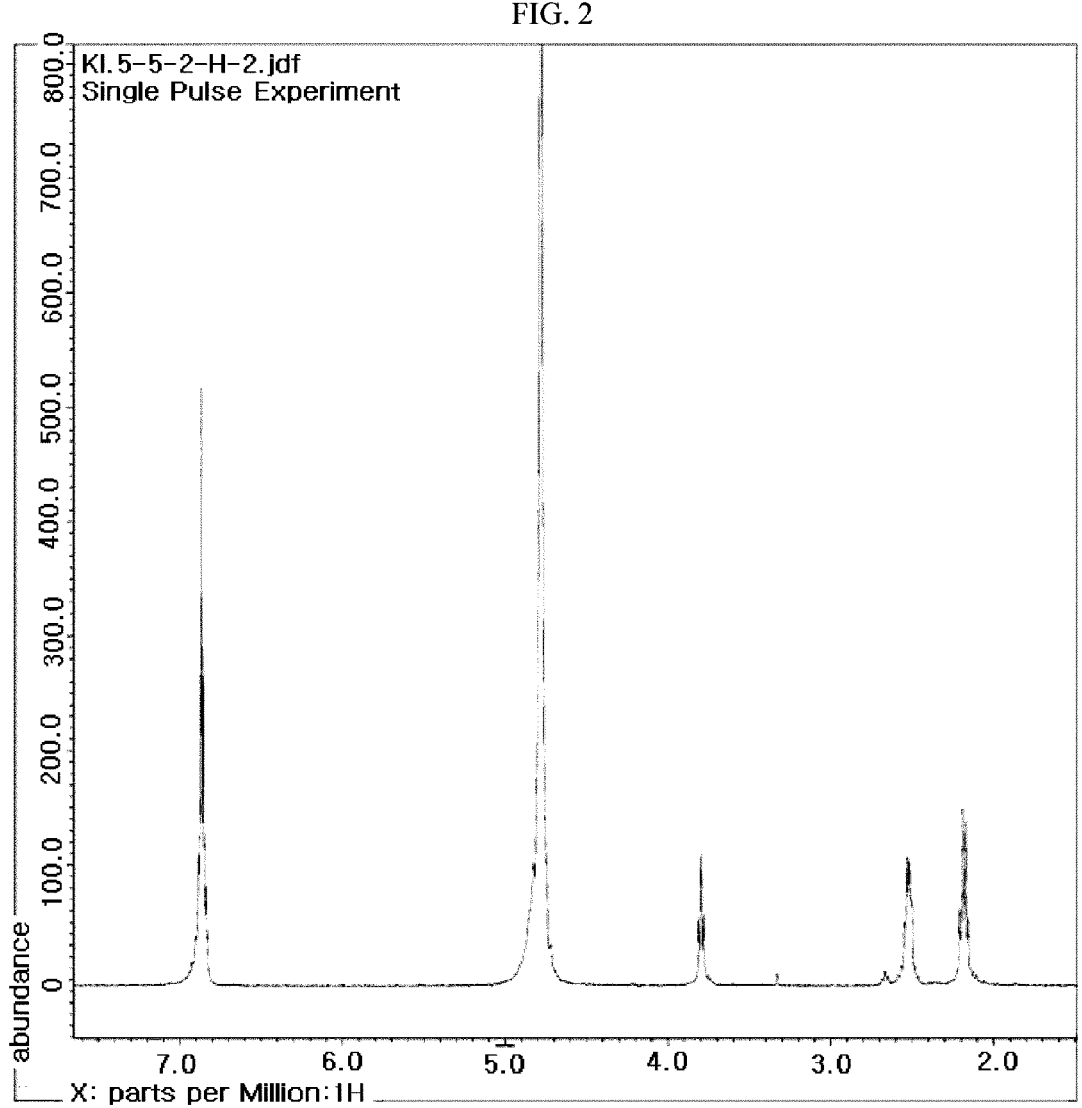
FIG. 2 shows the $^1$H NMR spectrum of the RAMALIN™ according to the present invention.
Figure 3:
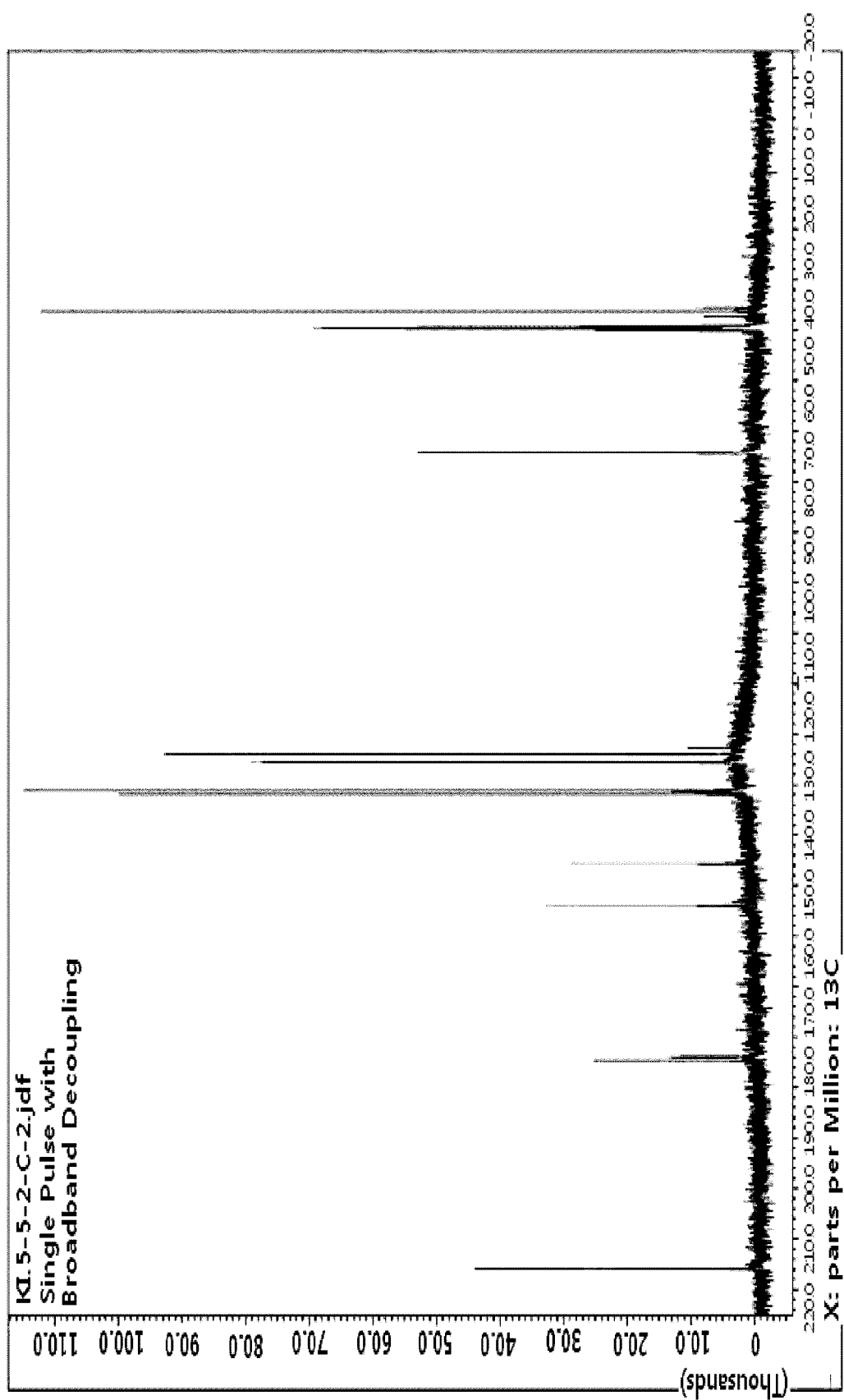
FIG. 3 shows the $^{13}$C NMR spectrum of the RAMALIN™ according to the present invention.

As a result, as shown in FIG. 1, in the positive mode of high-resolution ES-MS, the compound was shown to be a compound having a molecular weight of 254.1141 and a molecular formula of $C_{11}H_{16}N_3O_4$ consisting of 11 carbon atoms, 16 hydrogen atoms, 3 nitrogen atoms and 4 oxygen atoms. The data were confirmed again through the $^1H$ NMR and $^{13}C$ NMR spectra of the compound, and the compound was found to have a structure of the following formula 1 (FIGS. 2 and 3):

[Formula 1]

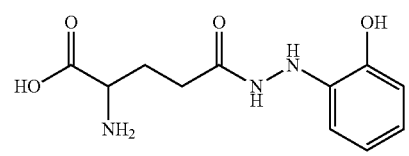 [SMILES: NC(CCC(=O)NNc1ccccc1O)C(=O)O]

Example 4

Measurement of Antioxidant Activity of RAMALIN™

(1) DPPH Free-Radical Scavenging Activity

The DPPH free-radical scavenging activity of the RAMALIN™ was measured using a modification of the method of Blois (Blois, M. S., Nature, 26:1199, 1958). For this purpose, a solution of 0.1 mmol of 1.1-diphenyl-2-picryl-hydazil (DPPH) in methanol was prepared, and 250 μL of the DPPH solution was mixed with 750 μL of each of RAMALIN™ solutions, obtained by dissolving the RAMALIN™ in methanol at various concentrations (0-10 μg/mL). Each of the mixture solutions was allowed to react at room temperature for 30 minutes. In order to measure the content of DPPH free radicals in each of the reaction mixtures, the absorbance of each solution at 517 nm was measured using a UV-visible spectrophotometer (SCINCO-AMERICA). As a positive control, solutions obtained by dissolving BHA (butylated hydroxyanisole) at various concentrations were used, and as a negative control, a test sample containing no reaction mixture was used. A decrease in the absorbance of the reaction mixture indicates an increase in the free-radical scavenging activity of the extract. All the experiments were repeated three times.

Figure 4:
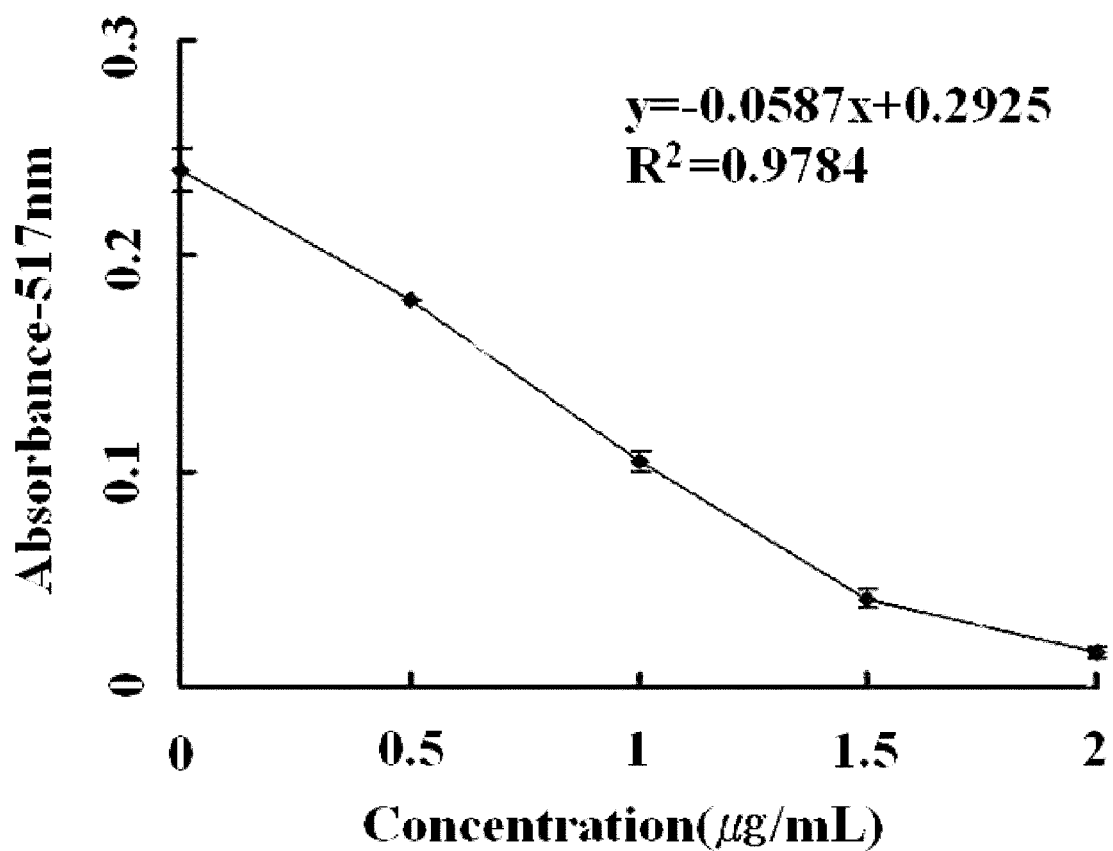
FIG. 4 shows the results of analyzing the DPPH free-radical scavenging ability of the RAMALIN™ according to the present invention.

As a result, as shown in FIG. 4, the DPPH free-radical scavenging activity of the RAMALIN™ Ramalin was concentration-dependent, the $IC_{50}$ value of the RAMALIN™ was 0.99±0.08 µg/mL, and the $IC_{50}$ value of the BHA was 4.97±0.9 µg/mL. Such results indicate that the DPPH free-radical scavenging activity of the RAMALIN™ is about 5 times higher than that of the positive control BHA.

(2) Measurement of $ABTS^{·+}$ Scavenging Activity

The $ABTS^{·+}$ scavenging activity of the RAMALIN™ was measured in comparison with that of the commercially available water-soluble vitamin E analogue Trolox (6-hydroxy-2,5,7,8-tetramethylchroman-2-carboxilic acid) (Rice-Evans, C. and Miller, N.J., *Meth. Enzymol.*, 234:279, 1994). For this purpose, 0-40 µg/mL of the RAMALIN™ was applied to a free radical (cation) production system containing 280 µL of a reaction mixture, described in the protocol of an antioxidant analysis kit (Product code CS0790, Sigma, USA). The amount of green color developed in the reaction mixture was measured at 405 nm using a spectrophotometer. The experiment was repeated three times, and a test sample containing no reaction mixture was used as a negative control.

Figure 5:
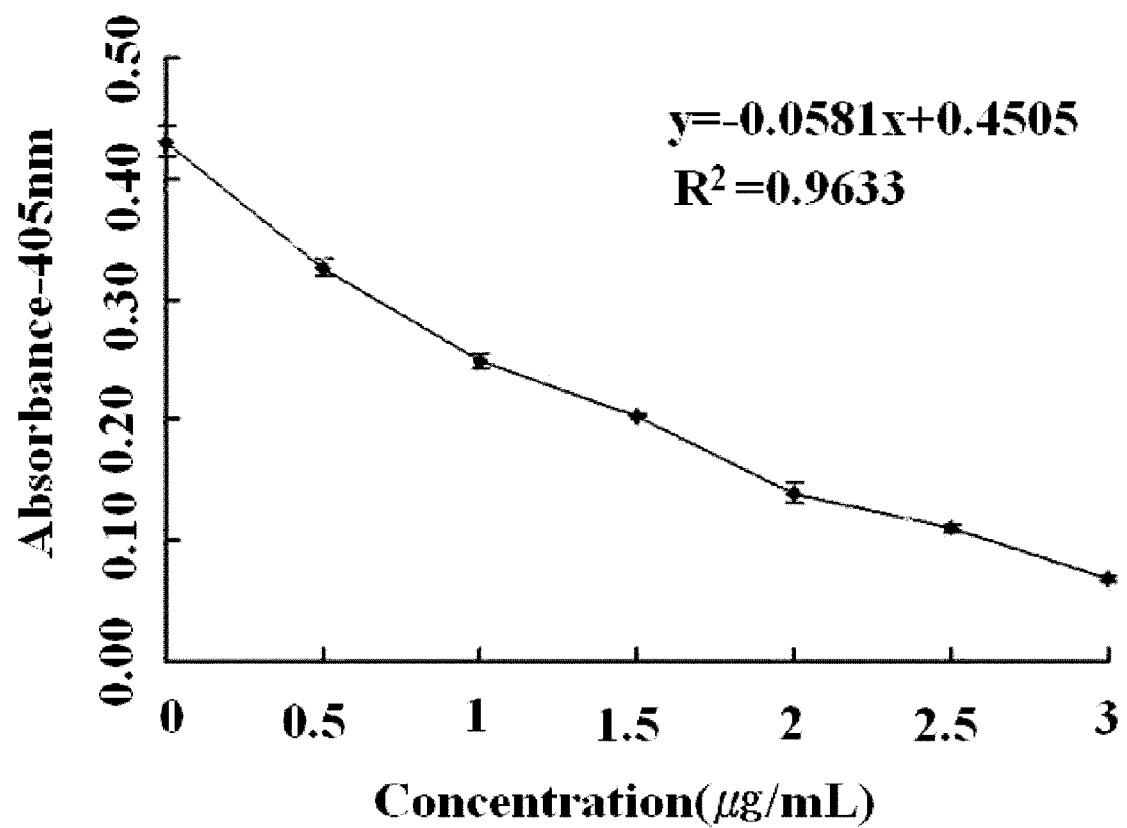
FIG. 5 shows the results of analyzing the ABTS free-radical scavenging ability of the RAMALIN™ according to the present invention.

As a result, as shown in FIG. 5, the $ABTS^{·+}$ scavenging activity of the RAMALIN™ was concentration-dependent, the $IC_{50}$ value of the RAMALIN™ was 1.7±0.2 µg/mL, and the $IC_{50}$ value of Trolox was 46.35±5.1 µg/mL. Such results indicate that the $ABTS^{·+}$ scavenging activity of the RAMALIN™ is about 27 times higher than that of the positive control BHA.

(3) Analysis of Reducing Ability

The reducing ability of the RAMALIN™ was measured using a slight modification of the method of Oyzaizu (Oyaizu, M., *Jpn. J. Nutr.*, 44:307-315, 1986). For this purpose, 100 µL of each of 0-20 µg/mL RAMALIN™ solutions was mixed with 250 µL of phosphate buffer (0.2 mol/L, pH 6.6) and 250 µL of potassium ferricyanid (10 g/L). Each of the reaction mixtures was allowed to react at 50° C. for 20 minutes, and then 150 µL of trichloroacetic acid (100 g/L) was added thereto. Then, 750 µL of $FeCl_3$ (1 g/L) was added slowly to the reaction mixture, after which the absorbance of the reaction mixture at 700 nm was measured. As a positive control, BHT (butylated hydroxytoluene) was used, and as a negative control, a test sample containing no reaction mixture was used. The experiment was repeated three times.

Figure 6:
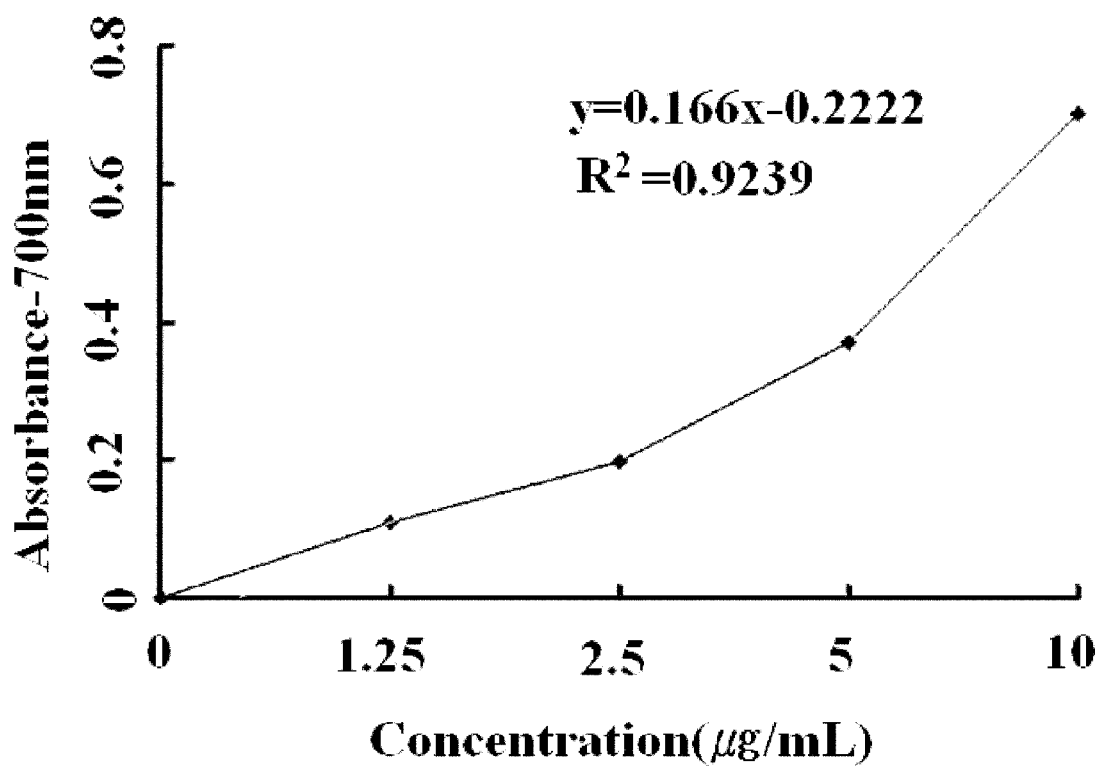
FIG. 6 shows the results of analyzing the $Fe^{+3}$-reducing activity of RAMALIN™ according to the present invention.

As a result, as shown in FIG. 6, the RAMALIN™ reduced $Fe^{+3}$ to $Fe^{+2}$ ion a concentration-dependent manner, and 1 µg of BAT showed the same reducing ability as 0.04 µg of the RAMALIN™. This suggests that the RAMALIN™ has a reducing ability higher than the commercially available antioxidant.

(4) Measurement of Superoxide Anion Scavenging Activity

The superoxide anion scavenging activity of the RAMALIN™ was measured according to the method of Beauchamp and Fridovich in comparison with various concentrations of BHA (butylated hydroxyanisole) (Beauchamp, C. and Fridovich, I., *Anal. Biochem.*, 44:276, 1971).

For this purpose, 50 mM phosphate buffer (pH 7.6), 20 µg of riboflavin, 12 mM EDTA, 0.1 mg of NBT and 0-20 µg of the RAMALIN™ were mixed with each other to prepare a reaction mixture. The reaction mixture was exposed to light for 3 minutes, and then covered with a blanket so as to be maintained under a dark condition. The decreased absorbance of the reaction mixture at 590 nm was measured, thus confirming the increased superoxide scavenging activity of the RAMALIN™. A test sample containing no reaction mixture was used as a negative control. The experiment was repeated three times.

Figure 7:
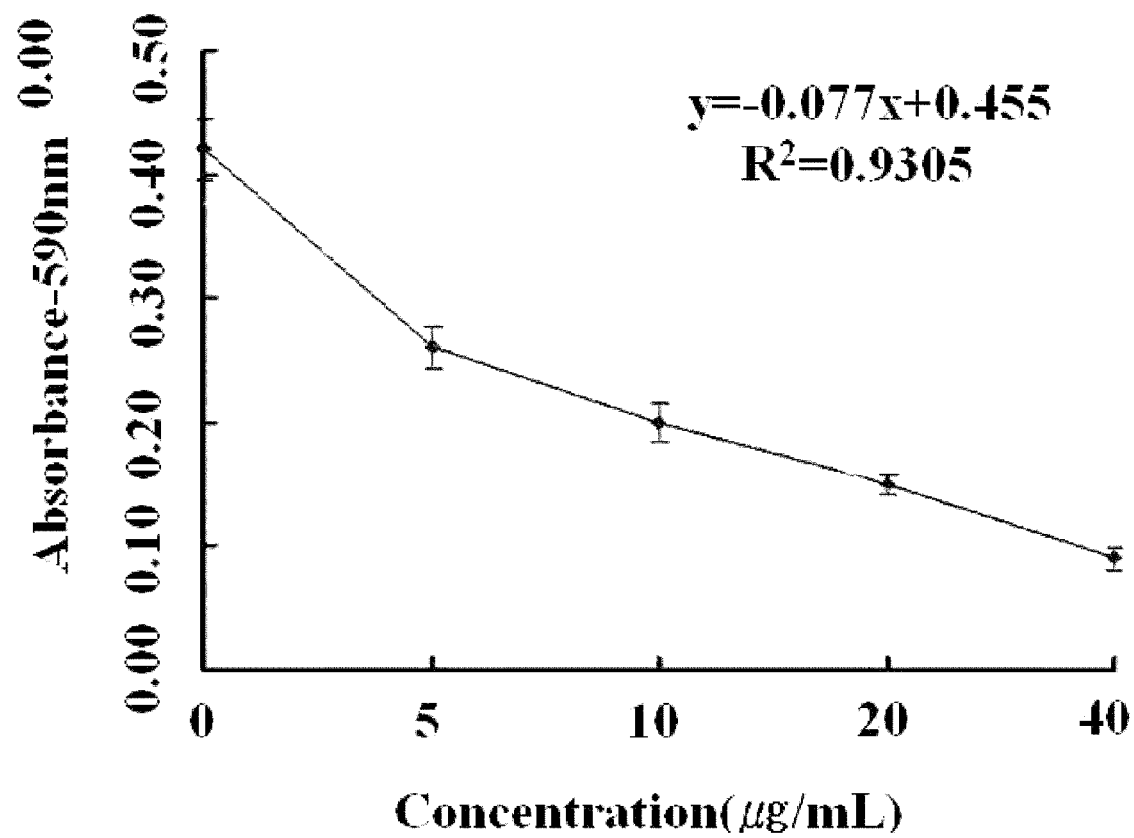
FIG. 7 shows the results of analyzing the superoxide scavenging activity of the RAMALIN™ according to the present invention.

As a result, as shown in FIG. 7, the RAMALIN™ inhibited the formation of blue formazan in a concentration-dependent pattern, the $IC_{50}$ value of the RAMALIN™ was 10.2±1.2 µg/mL, and the $IC_{50}$ value of the commercially available ascorbic acid was 12.7±1.2 µg/mL. This suggests that the superoxide anion scavenging activity of the RAMALIN™ is higher than the commercially available control group.

(5) Analysis of Tyrosinase Inhibitory Activity

The tyrosinase inhibitory activity of the RAMALIN™ was measured using a slight modification of the method of Higuchi (Higuchi, M. et al., *Planta Med.*, 59:253, 1993). For this purpose, 333 µL of 0.1 M phosphate buffer (pH 6.8), 165 µL of 0.5 mM L-DOPA solution, 333 µL of distilled water and 0-10 µg of the RAMALIN™ Ramalin were mixed with each other to prepare a reaction mixture, and 67 µL of mushroom tyrosinase (440 U/mL) was added thereto. Then, the reaction mixture was allowed to react at room temperature for 5 minutes, after which 33 µL of sodium azide (1 M) was added thereto to stop the reaction, and the absorbance of the mixture at 471 nm was measured. As a positive control, kojic acid was used, and as a negative control, a test sample containing no reaction mixture was used. The experiment was repeated three times.

Figure 8:
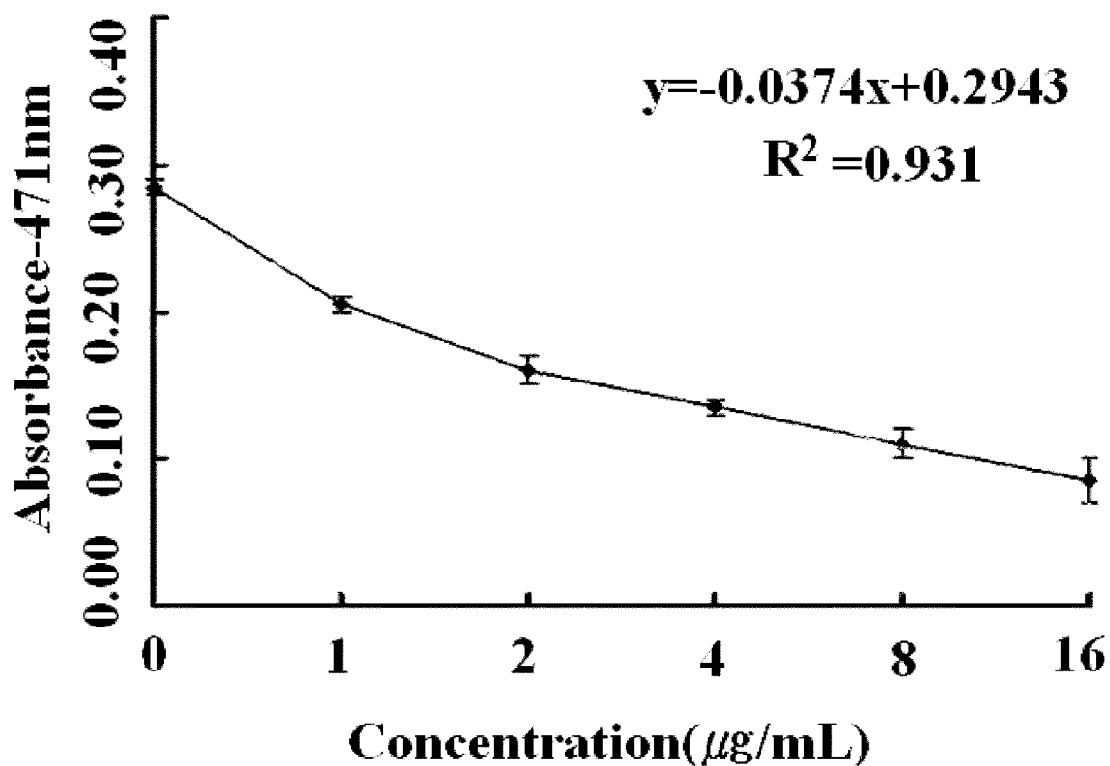
FIG. 8 shows the results of analyzing the tyrosinase inhibitory activity of the RAMALIN™ according to the present invention.

As a result, as shown in FIG. 8, the RAMALIN™ inhibited mushroom tyrosinase activity in a concentration-dependent pattern, the $IC_{50}$ value of the RAMALIN™ was 4±0.4 µg/mL, and the $IC_{50}$ value of the positive control kojic acid was 5±0.5 µg/mL. Such results indicate that the tyrosinase inhibitory activity of the RAMALIN™ is higher than that of the commercially available control group.

Example 5

Examination of the Ability to Suppress Oxidative Stress in Macrophages

Excessive oxidative stress induces the abnormal function of macrophages, resulting cell dysregulation. Thus, whether the RAMALIN™ shows antioxidant activity in murine macrophages was examined.

For this purpose, Raw264.7 cells (Korean Cell Line Bank, Seoul, South Korea) were cultured in DMEM medium (Gibco-BRL, USA), containing 10% FBS, 2 mM L-glutamine, 100 U/ml penicillin and 100 µg/ml streptomycin, in a 5% $CO_2$ incubator at 37° C. To stimulate the Raw264.7 cells, the cells were seeded into a 96-well plate at a concentration of $1 \times 10^6$ cells/well and cultured overnight. Then, the medium was replaced with a DMEM medium containing either the RAMALIN™ or 10 µM dexamethasone in the presence or absence of *E. coli* LPS (serotype O111:B4, Sigma, USA) or PMA (phorbol myristate acetate, Sigma, USA), and the cells were additionally cultured for 24 hours. The culture medium was used in a peroxide ($H_2O_2$) assay and a NO (nitric oxide) assay.

(1) Peroxide ($H_2O_2$) Assay

The intracellular production of $H_2O_2$ was measured according to the method of Roesler, C. et al. using DHR (Roesler, C. et al., *Int. J. Immunopharmacol*, 13:27-37, 1991).

While ROS are produced in cells, non-fluorescent DHR is oxidized by $H_2O_2$ and converted irreversibly into the green fluorescent compound rhodamine 123 (R123). R123 is a membrane-impermeable compound that is accumulated in cells.

10 μM of DHR was added to each well of a 96-well plate, containing the Raw264.7 cells cultured in the LPS- or PMA-containing medium, and was allowed to react at 37° C. for 30 minutes. The medium was replaced with a DMEM containing either the RAMALIN™ Ramalin (0.125 μg/ml, 0.25 μg/ml, 0.5 μg/ml and 1 μg/ml) or PBS, and the cells were allowed to react at 37° C. for 3 hours, after which the absorbance of each well at 488 nm was measured, thus determining the concentration of R123 in each well.

As a result, as can be seen in FIG. 9, the RAMALIN™ inhibited the secretion of $H_2O_2$ in a concentration-dependent manner.

(2) NO Assay

The medium was replaced with a DMEM containing the RAMALIN™ (0.5 μg/ml, 1 μg/ml and 2 μg/ml) or 10 μM dexamethasone in the presence or absence of LPS or PMA, and the cells were additionally cultured for 24 hours.

The production of nitrite in the culture medium was measured. For this purpose, 100 μl of the culture medium and the same amount of Griess reagent (containing 1% sulfanilamide and 0.1% N-1-naphylenediamine dihydrochloride in 2.5% phosphoric acid) were mixed with each other, and the mixture was allowed to react at room temperature for 10 minutes. The concentration of nitrite in the culture medium was determined by measuring the absorbance (OD) of the reaction mixture at 540 nm. The experiment was repeated three times.

As a result, as shown in FIG. 10, it could be seen that, when the RAMALIN™ Ramalin was added to the Raw264.7 activated with LPS, the secretion of NO (nitric oxide) in the cells was significantly reduced.

INDUSTRIAL APPLICABILITY

The RAMALIN™ according to the invention has significantly excellent antioxidant effects compared to commercially available antioxidants, and thus can be widely used in agents for treating oxidation-related diseases, anti-aging functional foods, functional cosmetic products for skin whitening and wrinkle reduction, etc.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A method for preparing a compound having the following structure:

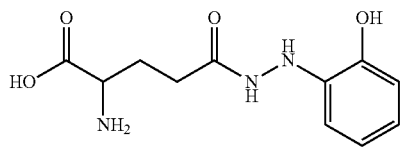 [SMILES: NC(CCC(=O)NNc1ccccc1O)C(=O)O]

wherein the method comprises:

(a) extracting dried *Ramalina terebrata* with a polar solvent selected from water, a $C_1$-$C_4$ lower alcohol and a mixed solvent thereof, thereby obtaining a crude extract;

(b) extracting the crude extract with a non-polar solvent selected from hexane, chloroform, benzene, carbon tetrachloride and pentane, thereby removing a non-polar solvent fraction which is extracted with the non-polar solvent; and (c) subjecting the extract, from which the non-polar solvent fraction has been removed, to liquid chromatography, thereby obtaining a fraction showing antioxidant activity.

2. An antioxidant composition comprising:

a compound having the following structure or a pharmaceutically acceptable salt thereof;

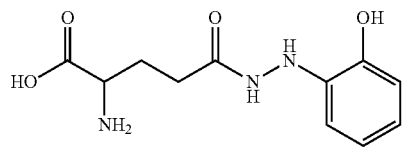 [SMILES: NC(CCC(=O)NNc1ccccc1O)C(=O)O]

a pharmaceutically acceptable carrier.

3. A method of treating an oxidation-related disease comprising administering the antioxidant composition of claim 2 to a subject in need of such treatment.

4. The method according to claim 3, wherein the oxidation-related disease is selected from the group consisting of cancer, aging, coronary arteriosclerosis, diabetes, epilepsy, and neurodegenerative disease.

5. A functional cosmetic composition comprising:

a compound having the following structure:

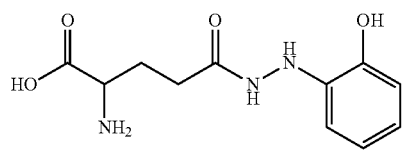

and a carrier.

6. A method of whitening skin or reducing skin wrinkling, the method comprising administering the cosmetic composition according to claim 5 to a subject in need of such treatment.

* * * * *

UNITED STATES PATENT AND TRADEMARK OFFICE
CERTIFICATE OF CORRECTION

| | | |
|---|---|---|
| PATENT NO. | : 8,809,578 B2 | Page 1 of 2 |
| APPLICATION NO. | : 13/128586 | |
| DATED | : August 19, 2014 | |
| INVENTOR(S) | : Joung Han Yim | |

It is certified that error appears in the above-identified patent and that said Letters Patent is hereby corrected as shown below:

On title page 1, at item (75) Inventors at line 8, change "(KP);" for Yoo Kyung Lee to --(KR);--.

In column 2 (page 1, item 56) at line 20, under Other Publications, change "Platismatica" to --Platismatia--.

In column 1 (page 2, item 56) at line 8, under Other Publications, change "Platismatica" to --Platismatia--.

In column 1 (page 2, item 56) at line 14, under Other Publications, change "partitiion" to --partition--.

In column 1 (page 2, item 56) at line 17, under Other Publications, change "20672073" to --2067-2073--.

In column 1 (page 2, item 56) at line 21, under Other Publications, change "Platismatica" to --Platismatia--.

In column 1 (page 2, item 56) at line 26, under Other Publications, change "licen" to --lichen--.

In column 1 at line 1, change "RAMALIN" to --RAMALIN™--.

In column 1 at line 20, change "hypocholorous" to --hypochlorous--.

In column 1 at line 63, change "naphtoquinones, usninic" to --naphthoquinones, usnic--.

In column 4 at line 17, change "ABTS" to --$ABTS^+$--.

In column 5 at line 11, change ""partenteral"" to --"parenteral"--.

In column 7 at line 18, change "45-50° C" to --45~50° C--.

In column 9 at line 15 (approx.), change "carboxilic" to --carboxylic--.

In column 9 at line 38, change "ferricyanid" to --ferricyanide--.

In column 10 at line 18 (approx.), change "RAMALIN™ Ramalin" to --RAMALIN™--.

Signed and Sealed this
Fifteenth Day of March, 2016

Michelle K. Lee
*Director of the United States Patent and Trademark Office*

CERTIFICATE OF CORRECTION (continued)

In column 11 at line 5, change "RAMALIN™ Ramalin" to --RAMALIN™--.

In column 11 at line 21, change "naphylenediamine" to --naphthylenediamine--.

In column 11 at line 28, change "RAMALIN™ Ramalin" to --RAMALIN™--.

In column 12 at line 26 (approx.), in Claim 2, after " 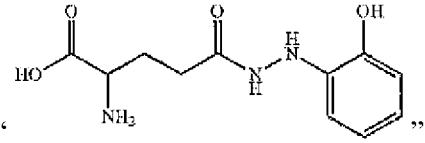 " insert --and--.